United States Patent [19]

Schäfer

[11] Patent Number: 4,966,996

[45] Date of Patent: Oct. 30, 1990

[54] PROCESS FOR THE PREPARATION OF E-2-PROPYL-2-PENTENOIC ACID AND PHYSIOLOGICALLY COMPATIBLE SALTS THEREOF

[75] Inventor: Helmut Schäfer, Kayhude, Fed. Rep. of Germany

[73] Assignee: Desitin Arznemittel GmbH, Hamburg, Fed. Rep. of Germany

[21] Appl. No.: 203,293

[22] Filed: Jun. 2, 1988

[30] Foreign Application Priority Data

Jun. 2, 1987 [DE] Fed. Rep. of Germany ....... 3718801

[51] Int. Cl.$^5$ .................... C07C 27/02; C07C 51/41; C07C 57/03
[52] U.S. Cl. .................................. 562/598; 560/213
[58] Field of Search ................. 562/606, 598, 599; 560/213

[56] References Cited

U.S. PATENT DOCUMENTS

| | | | |
|---|---|---|---|
| 2,376,067 | 5/1945 | Long | 560/213 |
| 2,679,530 | 5/1954 | Porret | 560/213 |
| 4,337,209 | 6/1982 | Akers et al. | 562/606 |

FOREIGN PATENT DOCUMENTS

| | | | |
|---|---|---|---|
| 1186063 | 1/1965 | Fed. Rep. of Germany | 560/213 |
| 215533 | 11/1984 | Fed. Rep. of Germany | 562/606 |

OTHER PUBLICATIONS

Wagner et al., Synthetic Organic Chemistry, John Wiley & Sons, Inc., N.Y. 1953, p. 417.

*Primary Examiner*—Vivian Garner
*Attorney, Agent, or Firm*—Nixon & Vanderhye

[57] ABSTRACT

A novel process for the preparation of E-2-propyl-2-pentenoic acid, as well as the physiologically compatible salts thereof is described, in which 2-bromo-2-propyl-pentenoic acid ethyl ester is used as the starting compound. The bromine is split off with a cyclic tertiary amine in acetonitrile as the solvent and preferably the E-isomer of the ethyl ester is formed. The free acid is obtained by subsequent saponification under careful conditions and optionally, preferably using the corresponding carbon dioxide salts in aqueous acetone solution, is converted into the salt form.

3 Claims, No Drawings

PROCESS FOR THE PREPARATION OF E-2-PROPYL-2-PENTENOIC ACID AND PHYSIOLOGICALLY COMPATIBLE SALTS THEREOF

E-2-propyl-2-pentenoic acid, a derivative of valproic acid, has of late awakened considerable interest as a possible therapeutic for the treatment of epilepsy. Thus, whereas in the case of a conventional treatment with valproic acid heptotoxic and teratogenic characteristics are to be feared in certain cases, comparative animal test with E2-propyl-2-pentenoic acid reveal that, with an at least equivalent therapeutic activity, it leads to no heptotoxic or teratogenic effects (cf. W. Loscher, Drugs of the Future, 10, pp. 389–391). The toxicologically favourable characteristics are particularly observed in the case of the E-isomer of 2-propyl-2-pentenoic acid.

E-2-propyl-2-pentenoic acid is a crystalline compound with a melting point of 38° to 40° C. and which has long been known as such.

One way of preparing the compound leads, according to a known process, from 2-bromo-2-propyl pentanoic acid or a derivative thereof as starting products, via the splitting off of HBr by means of an alkaline compound, preferably a tertiary amine at temperatures above 100° C., to 2-propyl-2-pentenoic acid. A disadvantage of this process is that varying quantities of the Z and E-isomers are formed during the splitting off of HBr and they are usually additionally contaminated by 2-propyl-3-pentenoic acid formed by the migration of the double bond.

The problem of the present invention is therefore to provide a process in which the formation of the E-isomer of 2-pentenoic acid is favoured.

The process according to the present invention is proposed for solving this problem It has suprisingly been found that in preferred manner the E-isomer of 2-propyl-2-pentenoic acid ethyl ester is formed if the splitting off of the bromine from the starting compound 2-bromo-2-propyl pentanoic acid ethyl ester takes place in accordance with the following Formulas II and III

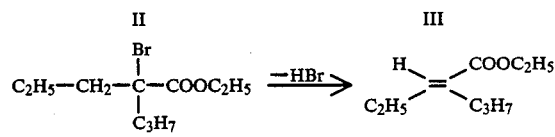

using a cyclic tertiary amine and performed in the presence of acetonitrile as the solvent. According to the invention, preferably triethylene diamine is used as the cyclic tertiary amine.

Splitting off is carried out by refluxing the reaction mixture for several hours, preferably 6 to 10 hours. When using triethylene diamine as the tertiary amine, said amine is obtained in crystalline form during the boiling of the HBr salt and can be separated to recover the triethylene diamine.

Prior to the conventional working up of the reaction micture, a large part of the acetonitvile used is recovered by distillation. The residue is dissolved in water and after acidification the ester is separated using an organic solvent and is purified by distillation.

Preferably the separation of the E-isomer takes place, e.g., by precision distillation in said process stage. However, separation can also take place following the subsequently explained reaction to the free acid.

The ester is carefully saponified for preparing the free acid. This can, e.g., take place at room temperature with sodium hydroxide in methanol as the solvent. The mixture is allowed to stand for a few days, preferably 4 to 6 days and, after acidifying the solution, the free acid is obtained in conventional manner, e.g., by distillation, whilst recovering the methanol. Small amounts of E-2-propyl-3-pentenoic acid can be separated from the desired derivative by conventional processes, e.g., by precision distillation.

If desired, the free acid can be converted in conventional manner into the form of a physiologically compatible salt.

According to a particularly preferred embodiment the reaction is performed in aqueous acetone as the solvent in the presence of the corresponding carbon dioxide salt. If, e.g., the sodium salt of E-2-propyl-2-pentenoic acid is to be prepared, then preferably sodium carbonate in a solution of the free acid is refluxed for a few hours in an acetone/water mixture. After cooling to a temperature below 0° C., the sodium salt is obtained as a precipitate of fine white crystals.

The invention is illustrated hereinafter by means of examples.

EXAMPLE 1

Preparation of 2-propyl-2-pentenoic acid ethyl ester

A solution of 100 g of triethylene diamine (1,4-diazabicyclo[2,2,2]-octane) in 400 ml of acetonitrile are added to a solution of 100 g of 2-bromo-2-propyl pentanoic acid ethyl ester in 200 ml of acetonitrile. The colourless reaction mixture is refluxed for 8 hours and precipitation of a white salt starts after only 15 minutes. Subsequently approximately 450 ml of acetonitrile are distilled off and recovered on the rotary evaporator at 200 mbar and 40° C. The oily-crystalline residue is mixed with 1000 ml of water, accompanied by the dissolving of the separated salt. After acidifying with 1N hydrochloric acid to pH 1, the separated oil is taken up in 150 ml of n-hexane and the aqueous phase is extracted twice more with in each case 150 ml of n-hexane. After washing and drying the organic phase, distillation takes place. The yield is 54.3 g of a mixture of E and Z-2-propyl-2-pentenoic acid ethyl ester with a content of 42 g of the sought E-isomer, corresponding to 62% based on the starting product.

EXAMPLE 2

Preparation of 2-propyl-2-pentenoic acid 10 g of 2-propyl-2-pentenoic acid ethyl ester according to Example 1 are added to a solution of 20 g of sodium hydroxide in 150 ml of methanol and left stand at room temperature. After 5 days and accompanied by the recovery of the methanol, the mixture is worked up in conventional manner following acidification. A mixture of 2-propyl-2-pentenoic acid (E-isomer) and 2-propyl-3-pentenoic acid (E-isomer) in a ratio of approximately 80:20 is obtained in an almost quantitative yield, which is separated by precision distillation on an effective column and gives E-2-propyl-2-pentenoic acid with $b.p._{15}$ 135° to 136° C.

EXAMPLE 3

Preparation of E-2-propyl-2-pentenoic acid sodium salt 10 g of finely ground, anhydrous sodium carbonate are refluxed for 6 hours in a solution of 142.2 g of E-2-propyl-2-pentenoic acid in 1600 ml of acetone and 54 ml of water and the solution is subsequently filtered. The sodium salt crystallizes out of the filtrate in the form of fine, white crystals following cooling to approximately −5° C. After working up the mother liquor, the yield is almost quantitative. The melting point of the crystals formed is above 300° C. and the salt obtained is easy to dissolve in water.

I claim:

1. Process for preparing E-2-propyl-2-pentenoic acid of the formula:

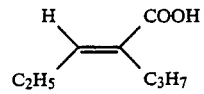

comprising reacting 2-bromo-2-propyl-pentanoic acid ethyl ester of the formula:

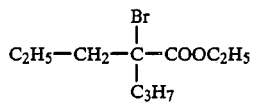

at elevated temperature with triethylene diamine in acetonitrile as the solvent to remove HBr from the acid ethyl ester and thereafter converting the ester by saponification to form E-2-propyl-2-pentenoic acid.

2. The process of claim 1, in which the E-2-propyl-2-pentenoic acid is converted to a physiologically compatible salt by reacting the free E-2-propyl-2-pentenoic acid with the corresponding salt of carbon dioxide in a mixture of acetone and water as the solvent.

3. The process of claim 2, in which sodium carbonate is used as the carbon dioxide salt.

* * * * *